(12) United States Patent
Walker et al.

(10) Patent No.: US 10,945,661 B2
(45) Date of Patent: Mar. 16, 2021

(54) PHYSIOLOGICAL FEEDBACK SYSTEMS AND METHODS

(71) Applicant: Physio-Control, Inc., Redmond, WA (US)

(72) Inventors: Robert G. Walker, Seattle, WA (US); Fred W. Chapman, Newcastle, WA (US)

(73) Assignee: Physio-Control, Inc., Redmond, WA (US)

( * ) Notice: Subject to any disclaimer, the term of this patent is extended or adjusted under 35 U.S.C. 154(b) by 180 days.

(21) Appl. No.: 15/960,324

(22) Filed: Apr. 23, 2018

(65) Prior Publication Data

US 2018/0303411 A1 Oct. 25, 2018

Related U.S. Application Data

(60) Provisional application No. 62/489,029, filed on Apr. 24, 2017, provisional application No. 62/488,678, filed on Apr. 21, 2017.

(51) Int. Cl.

| | |
|---|---|
| *A61B 5/00* | (2006.01) |
| *A61B 5/1455* | (2006.01) |
| *A61B 5/083* | (2006.01) |
| *A61B 5/0205* | (2006.01) |
| *A61B 5/085* | (2006.01) |

(Continued)

(52) U.S. Cl.
CPC ............ *A61B 5/486* (2013.01); *A61B 5/0836* (2013.01); *A61B 5/14551* (2013.01); *A61B 5/4836* (2013.01); *A61H 31/004* (2013.01); *A61H 31/005* (2013.01); *A61B 5/0002* (2013.01); *A61B 5/0205* (2013.01); *A61B 5/0452* (2013.01); *A61B 5/085* (2013.01); *A61B 5/7275* (2013.01); *A61B 5/742* (2013.01); *A61H 2201/501* (2013.01); *A61H 2230/045* (2013.01); *A61H 2230/065* (2013.01);

(Continued)

(58) Field of Classification Search
CPC ... A61B 5/0205; A61B 5/0452; A61B 5/0836; A61B 5/14551; A61B 5/4836; A61B 5/486; A61B 5/7275; A61B 5/0002; A61B 5/085; A61B 5/742; A61H 31/004; A61H 31/005; A61H 2230/045; A61N 1/3904; A61N 1/3925; A61N 1/36521; A61N 1/37
See application file for complete search history.

(56) References Cited

U.S. PATENT DOCUMENTS

| | | | | |
|---|---|---|---|---|
| 8,152,732 B2* | 4/2012 | Lynn | ........................ | A61B 5/00 600/529 |
| 8,187,201 B2* | 5/2012 | Lynn | ...................... | A61B 7/003 600/538 |

(Continued)

Primary Examiner — Christopher A Flory
(74) Attorney, Agent, or Firm — Lee & Hayes, P.C.

(57) ABSTRACT

The disclosed physiological feedback systems and methods assist with assessing, monitoring and/or treating a patient experiencing a cardiac arrest event. The systems and methods receive multiple inputs and are continuous and/or iterative during a treatment session to provide physiological state trends of the patient. An index of the physiological state of the patient can be derived and confounders, and/or their effects, can be identified, and/or removed, from the index. Additionally, the systems and methods can assist with determining ischemic injury in a patient based on cerebral tissue oxygenation and/or other physiological data.

20 Claims, 9 Drawing Sheets

(51) Int. Cl.
*A61N 1/39* (2006.01)
*A61N 1/365* (2006.01)
*A61N 1/37* (2006.01)
*A61B 5/0452* (2006.01)
*A61H 31/00* (2006.01)

(52) U.S. Cl.
CPC ............ *A61N 1/36521* (2013.01); *A61N 1/37* (2013.01); *A61N 1/3904* (2017.08)

(56) References Cited

U.S. PATENT DOCUMENTS

| | | | | |
|---|---|---|---|---|
| 8,241,213 B2* | 8/2012 | Lynn | ........................ | A61B 5/00 600/301 |
| 8,728,001 B2* | 5/2014 | Lynn | ........................ | A61B 5/002 600/529 |
| 8,862,196 B2* | 10/2014 | Lynn | ........................ | A61B 7/003 600/323 |
| 8,932,227 B2* | 1/2015 | Lynn | ........................ | A61B 7/003 600/484 |
| 9,042,952 B2* | 5/2015 | Lynn | ........................ | G16H 40/63 600/324 |
| 9,468,378 B2* | 10/2016 | Lynn | ........................ | A61B 5/00 |
| 9,521,971 B2* | 12/2016 | Lynn | .................. | A61B 5/14552 |
| 10,058,269 B2* | 8/2018 | Lynn | ........................ | A61B 7/003 |
| 2005/0203352 A1* | 9/2005 | Al-Ali | .................. | A61B 5/7221 600/309 |
| 2007/0191697 A1* | 8/2007 | Lynn | .................. | A61B 5/0205 600/323 |
| 2009/0131805 A1* | 5/2009 | O'Brien | ............ | A61B 5/02028 600/485 |
| 2009/0281838 A1* | 11/2009 | Lynn | ........................ | G16H 50/20 705/3 |
| 2011/0015501 A1* | 1/2011 | Lynn | ........................ | A61B 5/00 600/301 |
| 2011/0208539 A1* | 8/2011 | Lynn | ........................ | A61B 7/003 705/2 |
| 2012/0302845 A1* | 11/2012 | Lynn | .................... | A61B 5/0205 600/323 |
| 2013/0060110 A1* | 3/2013 | Lynn | ........................ | A61B 7/003 600/324 |
| 2013/0218600 A1* | 8/2013 | Lynn | ........................ | G06Q 50/24 705/3 |
| 2013/0276785 A1* | 10/2013 | Melker | ................ | A61M 5/1723 128/204.23 |
| 2013/0338459 A1* | 12/2013 | Lynn | .................. | A61B 5/14552 600/323 |
| 2014/0152673 A1* | 6/2014 | Lynn | .................. | A61B 5/14551 345/473 |
| 2014/0163897 A1* | 6/2014 | Lynn | .................... | A61B 5/0205 702/19 |
| 2014/0288953 A1* | 9/2014 | Lynn | .................. | A61B 5/14551 705/2 |
| 2014/0365175 A1* | 12/2014 | Packer | ................. | A61B 5/0402 702/182 |
| 2015/0045686 A1* | 2/2015 | Lynn | ...................... | A61B 7/003 600/531 |
| 2015/0087936 A1* | 3/2015 | Al-Ali | .................. | A61B 5/0205 600/309 |
| 2016/0067499 A1* | 3/2016 | Owen | ................ | A61B 5/02416 600/324 |
| 2016/0133160 A1* | 5/2016 | Packer | .................. | G16H 40/67 600/509 |
| 2016/0135706 A1* | 5/2016 | Sullivan | ............... | A61B 5/0059 600/301 |
| 2016/0199252 A1* | 7/2016 | Freeman | ................ | A61H 31/00 601/41 |
| 2016/0256350 A1* | 9/2016 | Johnson | ............ | A61N 1/3925 |
| 2016/0302704 A9* | 10/2016 | Lynn | .................. | A61B 5/14552 |
| 2016/0317385 A1* | 11/2016 | Salcido | ............... | A61H 31/005 |
| 2016/0378952 A9* | 12/2016 | Lynn | ...................... | G16H 50/70 705/3 |
| 2017/0065484 A1* | 3/2017 | Addison | ............ | A61B 5/0205 |
| 2017/0079530 A1* | 3/2017 | DiMaio | ................ | A61B 5/0075 |
| 2017/0105644 A1* | 4/2017 | Sullivan | .................. | A61B 5/04 |
| 2017/0105898 A1* | 4/2017 | Taylor | .................. | A61H 31/008 |
| 2017/0120063 A1* | 5/2017 | Freeman | ............ | A61B 5/0402 |
| 2017/0189265 A1* | 7/2017 | Freeman | ............ | A61N 1/3625 |
| 2017/0224581 A1* | 8/2017 | Johnson | ............ | G06F 19/3481 |
| 2017/0266399 A1* | 9/2017 | Campana | ............ | A61B 5/7282 |
| 2017/0367580 A1* | 12/2017 | DiMaio | ................ | A61B 5/0064 |
| 2017/0367618 A1* | 12/2017 | Ricciardelli | ......... | G01N 33/497 |
| 2018/0125430 A1* | 5/2018 | Al-Ali | ................. | A61B 5/7246 |
| 2018/0133105 A1* | 5/2018 | Paradis | ................ | A61H 9/0078 |
| 2018/0153765 A1* | 6/2018 | Freeman | ............ | A61N 1/39044 |
| 2018/0206795 A1* | 7/2018 | Al-Ali | ................. | A61B 5/7405 |
| 2018/0256043 A1* | 9/2018 | Melker | ................ | A61B 5/0295 |
| 2018/0303367 A1* | 10/2018 | Sullivan | .................. | A61B 5/04 |
| 2018/0310828 A1* | 11/2018 | DiMaio | ................ | A61B 5/0075 |

* cited by examiner

PHYSIOLOGICAL FEEDBACK SYSTEMS AND METHODS

CROSS-REFERENCE TO RELATED APPLICATIONS

This patent application claims the benefit of and priority to U.S. Provisional Patent Application Ser. No. 62/488,678 filed on Apr. 21, 2017 entitled "Physiological Feedback System and Method to Support Cardiac Arrest Resuscitation Management," the contents of which are hereby incorporated by reference in their entirety.

This patent application also claims the benefit of and priority to U.S. Provisional Patent Application Ser. No. 62/489,029 filed on Apr. 24, 2017 entitled "CPR Feedback using Tissue Oxygenation Technologies," the contents of which are hereby incorporated by reference in their entirety.

BACKGROUND

During cardiac arrest, a patient is pulseless and in need of immediate life-saving treatment. Often, the first response is to begin administering cardiopulmonary resuscitation (CPR) to the patient to mechanically force blood through the patient. This mechanical circulation can move the patient's blood in an attempt to provide oxygen to the patient's organs to help keep the patient alive. To assist with the life-saving effect, one or more parameters of the administered CPR can be altered in an attempt to increase the efficacy of the CPR.

For patients in cardiac arrest, the current treatment protocol often requires that rescuers achieve a return of circulation prior to transporting the patient to a hospital. This requirement increases the likelihood that the patient is stable and/or ensuring the patient has a reasonable expectation of recovery from potential further treatment they later receive at the hospital. While the return of circulation is a clear threshold, it does not account for other potential factors that can indicate a likelihood of a positive clinical outcome for the patient.

There exists a need for physiological feedback systems and methods that help rescuers improve clinical outcomes for cardiac arrest patients.

DETAILED DESCRIPTION

Figure 1:
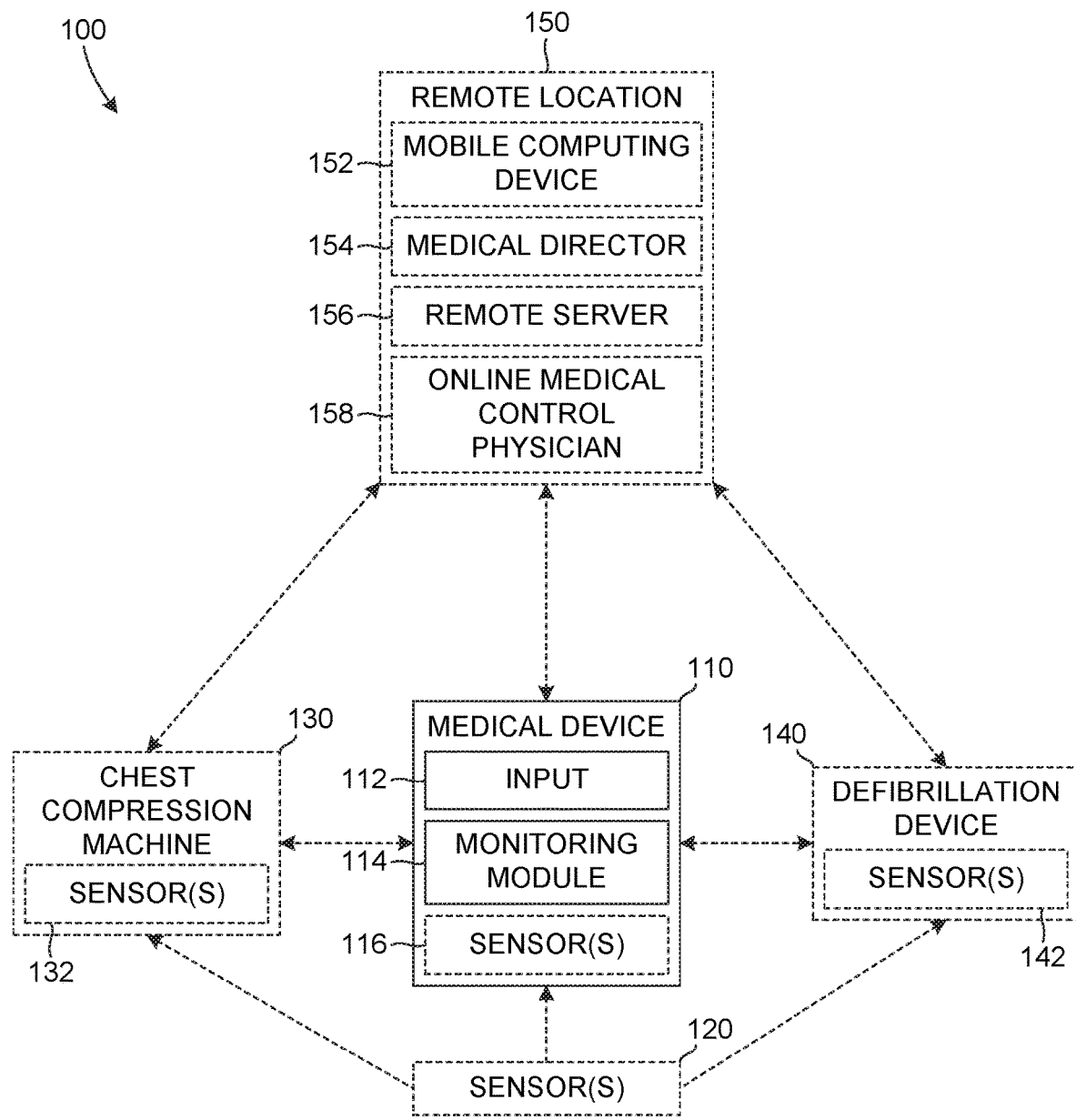
FIG. 1 is an example block diagram of a physiological feedback system.

Physiological feedback systems and methods are described herein. The described systems and methods assist rescuers, or others, in assessing the physiological state of the patient, and/or assessing the course of the patient's physiologic state over a patient care event, such as a resuscitation effort. For rescuers, the systems and methods can assist with predicting the Return of Spontaneous Circulation (ROSC), assessing the hemodynamic stability of the patient who has achieved ROSC for potential decline, and/or determining eligibility of the patient for more intensive resuscitation procedures that are only considered appropriate for a carefully-selected subset of patients. The described systems and methods can allow the rescuer to continuously monitor the physiological state of the patient and the effects of treatments performed thereon. The "whole picture" monitoring provided the rescuers can assist in determining the stability and/or transportability of the patient. Rather than relying on a singular or narrow criterion, the rescuer, and/or others, can be provided a comprehensive patient monitoring/treatment output from which further monitoring and/or treatment decisions can be made. Additionally, this iterative/continuous patient monitoring of the patient's physiological state can assist with assessing potential physiological damage of the patient caused by the event they are experiencing. This damage assessment can also be used to assist with determining further patient treatment and/or monitoring.

The systems and methods can use tissue oximetry and/or capnography data to provide feedback regarding monitoring and/or treatment of a patient. The feedback can include instructions to, and/or can be used to, alter, or otherwise change, the administration of treatment to the patient. For example, of one or more parameters of cardiopulmonary resuscitation (CPR) administration can be altered/changed based on the collected and/or analyzed tissue oximetry and/or capnography data. The tissue oximetry and/or capnography data can be used to derive an index to aid in the monitoring and/or treatment of the patient. Additionally, the tissue oximetry and/or capnography data can be used to determine the Return of Spontaneous Circulation (ROSC) and/or predict its likelihood. Further, the treatment and monitoring data can be correlated, such as by using the tissue oximetry and/or capnography data, to monitor the physiological effect of one or more treatments administered to the patient.

Further, the systems and methods described herein can identify potential confounders and their effects on the physiological state of the patient. Confounders are external influences, such as environmental influences, patient treatment influences, patient observations and/or other external inputs to the patient, that can obscure or influence the patient monitoring and/or treatment. Example confounders can include administration of medication that causes temporary changes in one or more physiological parameter measurements, unexpected patient observations, environmental factors and/or other inputs that can obscure a physiological state of the patient and/or the monitoring/treatment of the patient. The described systems and methods provide continuous and iterative patient monitoring that can assist with discriminating confounders and their influence in the patient monitoring. Confounders, and/or their effects, can be identified in the patient monitoring due to received information, such as patient physiological data, and/or by user input, such as observations and/or medication administrations. In addition to the multiple inputs that are processed and/or analyzed as part of the index, multiple confounders can also be accounted for. Additionally, both the confounders and/or other patient data can be accounted for in a time domain, allowing for the index to include temporal information that can assist with patient treatment and/or monitoring information.

FIG. 1 is an example patient treatment/monitoring system 100 that includes a medical device 110 that can be connected to and/or in communication with a sensor(s) 120, other patient monitoring and/or treatment devices/systems 130, 140, and/or a remote location 150. The medical device 110 can receive patient data from one or more sources and can provide regional tissue oximetry (rSO2) data—which describes the aggregate oxygenation state of the blood within a certain region of tissue—along with related data, to assist with patient monitoring and/or treatment. Using the patient data, the medical device 110 can display and/or provide information regarding the patient status. The medical device 110 can provide an increased accuracy and/or more comprehensive patient status by relating various patient physiological parameter and treatment data. In this manner, changes to the patient's physiological state can be more accurately assessed as an actual change in the patient's state or as a temporary change based on a treatment and/or other cause. The treatments and/or other causes are confounders, elements and/or inputs that cause, directly and/or indirectly, changes in the patient physiological data that obscure changes in the patient physiological data due to actual changes in the patient's physiological state. Accounting for, noting and/or removing the confounder effects on the patient physiological data allow for an increased accuracy in such data for assessment, monitoring and/or treating the patient. For example, administration of certain medications can cause a temporary and/or immediate increase in the $CO_2$ levels in the patient's blood, and thus the end-tidal $CO_2$ values measured by capnography. Such change in the physiological parameter data, capnography, of the patient, due to the medication administration, is short-term and/or temporary. A rescuer, device and/or system can monitor the capnography data and may misinterpret the temporary increase in $CO_2$ production as an indicator of patient improvement, and consequently may administer further patient monitoring and/or treatment based on this interpretation. By relating the physiologic parameter and treatment data, the system 100 can help the rescuer and/or device avoid misinterpreting such a change in one or more patient physiological parameters as an actual change in the patient state, rather than just an artifact of the medication administration.

The medical device 110 can include an input 112, a monitoring module 114 and/or a sensor(s) 116. To collect and/or receive patient data, the medical device can include the sensor(s) 116 and/or can communicate with other devices and/or systems, such as the sensor(s) 120, a chest compression machine 130, a defibrillation device 140, the remote location 150 and/or other external devices and/or systems. The collected and/or received patient data can include oximetry data, such as cerebral and/or other tissue oximetry data, and/or can include capnography data. The oximetry and/or capnography data can be analyzed and/or evaluated by the medical device 110 in correlation with the other received patient data, such as patient physiological and/or treatment data. Additionally, the medical device 110 can receive input 112 from a user and/or an external device/system. The input 112 can include patient treatment and/or observation data. For example, the input 112 can include data regarding medication administration, such as a medication identification, dosage, and/or other administration data and/or can include patient observation data, such as patient gasping, consciousness and/or purposeful movement, that can be provided by a user and/or device/system. Additionally, the input 112 can provide data regarding the weighting and/or importance of one or more of components of the patient data, such as a particular physiological parameter. Such input can be provided by a user, device and/or system. The medical device 110 can provide an output of the collected patient data that correlates the input and/or analyzed/evaluated oximetry/capnography data with other physiological and/or treatment data. In an example embodiment, this correlation can indicate that a change in a physiological parameter is a result of a change in the patient's physiological state or as a result of a confounder, such as a medication administration and/or a patient treatment.

The process of receiving and analyzing patient data can be a continuous and iterative process. This can allow the analysis and/or evaluation of patient data performed by the medical device 110 to be refined as patient treatment and/or monitoring continues. That is, events throughout the patient monitoring and/or treatment session can be used to refine analysis and/or evaluation of additional collected and/or received patient data to assist with patient monitoring and/or treatment. Using the repeated/continuous and/or iterative analysis and/or evaluation of patient data, the medical device 110 can provide trend data for one or more physiological parameters of the patient. The trend data can assist with and/or guide additional, or further, patient monitoring and/or treatment. Additionally, the trend data can reduce immediate and/or temporary changes to patient physiological parameter data so that decision making by a user, device and/or system can be based, at least in part, on trends in the data rather than solely on a real-time value of the data.

The medical device 110 provides an output that is a synthesis of patient data and/or inputs from one or more users, devices and/or systems. In this manner changes in the patient data can be evaluated based on an importance, effect, weight or other qualifier of one or more of the components of the patient data and/or the received inputs. That is, changes in the patient data can be validated with, and/or correlated, to changes in one or more components of the patient data and/or inputs. For example, a change in a first component of the patient data can be correlated to a change in a second component of the patient data and/or an input. Based on the correlation, the change in the first component of the patient data can be assessed and/or evaluated as a change in an actual patient state or can be assessed/evaluated as a change based on another factor, such as a change in treatment and/or administration of a medication. In this manner, the effect of changes in treatment of the patient can be evaluated for an associated impact on the physiological state of the patient.

Additionally, the multiple inputs to the medical device 110, to be used in generating the output, can include temporal data. This can allow the inputs, and/or their effects on the physiological state of the patient, to be evaluated spatially. That is, the timing of various treatments and/or their effects on the patient's physiological state can be accounted for in the generated output by the medical device 110

The monitoring module 114 can receive and/or collect patient physiologic data, including oximetry and/or capnography data, such as by the sensor(s) 116. Oximetry and/or capnography data can be tracked by the medical device 110 during the patient monitoring/treatment session and can provide data regarding the physiological state of the patient. While the real-time values of oximetry and/or capnography data can fluctuate, the trend of the oximetry/capnography data can be indicative of the trend of the patient physiological state. For example, oximetry/capnography values can be repeatedly changing, however, when analyzed/extracted as a trend, the oximetry/capnography trend can indicate changes to the patient physiological state over longer increments of time. The physiological parameters of oximetry and/or capnography are not only indicative of the patient physiological state, but are also parameters that exhibit correlation with each other. That is, increases in tissue oximetry are often accompanied by increased capnography measurements, as increased tissue oxygenation status during CPR is typically associated with increased blood flow which also causes increases in expired CO2. This correlation/relationship can allow the two parameters to validate each other and can also assist in validating, evaluating and/or assessing changes in other physiological parameters, such as changes in the patient electrocardiogram, blood pressure and/or other physiological parameters.

The medical device 110 can optionally include one or more sensors 116 to collect and/or receive patient data, such as physiological parameter data. Alternatively, or additionally, the medical device can be connected to and/or in communication with other sensors 120, other medical devices 130, 140, and/or one or more remote locations 150 to receive/collection patient data from. The collected and/or received patient data can be analyzed, evaluated and/or correlated by the medical device and/or other devices, to provide a comprehensive output that can assist with patient monitoring and/or treatment by a user, device and/or system. The comprehensive output can, or can assist with, identification of confounders in the patient data, such as changes in the patient data attributable to factors other than a change indicative of an improvement or a decline in a trend of the physiological state of the patient, such as in response to a treatment or lack thereof.

The output of the medical device 110 can assist with treatment and/or monitoring of the patient by a user and/or other devices/systems, such as 130, 140, 150. In an example, a user can be administering cardiopulmonary resuscitation (CPR) to a patient. The output of the medical device 110 can be, or can be used to assist with, CPR feedback. The user can receive the CPR feedback and can adjust, and/or receive instructions to adjust, the administration of the CPR to the patient to assist with increasing the efficacy of the administered CPR. While the CPR feedback can include comparison of the administered CPR to a CPR administration model, such as including a range of preferred chest compression depth and/or rate, the CPR feedback provided by, or based on, the output of the medical device 110 also compares, or accounts, for the effectiveness of the administered CPR by monitoring and/or analyzing trends in the collected/received patient data. For example, the effectiveness of the CPR and the feedback based thereon can be determined using one or more physiological parameters, such as tissue oximetry and/or capnography data. The tissue oximetry and/or capnography data can provide insight to the levels, or degree, of blood flow occurring in the patient which can be an indication of changes in the patient's physiological state and/or an indication of the effectiveness of administered treatments, including CPR for example or other treatments alone or in combination with administered CPR. If the output of the medical device 110 indicates that the patient's physiological state is declining despite the administration of the CPR, the medical device 110, the user, and/or other device/system can alter, and/or instruct/cause to be altered, the administration of the CPR to increase the effectiveness of the administered CPR treatment with regards to the patient's physiological state. Alteration of the administered CPR can include relocating the point, or area, on the patient to which compression force is being applied in the administration of CPR. The relationship between body surface landmarks and underlying vital organ structures is not identical between people, so repositioning of the location at which CPR compression force is being applied may facilitate an increase in the effectiveness of the administered CPR based on the patient's individual anatomy. Other alterations can include altering the depth, rate and/or other parameters of the administered CPR compressions. Further, much like the output of the medical device 110, such treatment feedback, such as CPR feedback, can also be an iterative process, with additional treatment alterations and/or additions instructed, or administered, based on the output of the medical device 110.

In addition to receiving information, such as patient data, from the one or more external users, devices and/or systems, the medical device 110 can also provide information, such as the output, to the external users, devices and/or systems. In the example shown in FIG. 1, the medical device 110 can communicate with other treatment/monitoring devices/systems, such as the chest compression machine 130 and/or defibrillation device 140. The chest compression machine 130 and/or the defibrillation device 140 can receive the output, or other information/instructions, from the medical device 110, which can alter the monitoring and/or treatment of the patient based on the received output, or other information/instructions.

The chest compression machine (CCM) 130 can administer chest compressions, such as part of a CPR treatment, to a patient and can include sensors 132, such as for monitoring the administration of compressions by the chest compression machine 130 and/or one or more physiological parameters of the patient. Additionally, or alternatively, the CCM 130 can receive patient physiological and/or other data from the optional sensor(s) 120. The chest compressions administered by the CCM 130 can have specific characteristics, including a depth of compression, a velocity of the administered compression, and/or a rate at which compressions are administered. Further, the CCM 130 can also administer active decompressions by actively lifting the patient's chest. The sensors 132 can transmit information to the medical device regarding the operation of the CCM 130 and/or the physiological state of the patient. The CCM 130 can also receive instructions from the medical device 110 to alter the administration of compressions by the CCM 130. The received instructions can automatically cause the CCM 130, and/or require at least some user input to cause the CCM 130, to alter the administration of compressions and/or active decompressions to the patient.

The CCM 130 can also communicate with one or more remote locations 150. The communication can include sending and receiving of information and/or instructions. That is, the remote location 150 can receive data from the CCM 130, such as sensor 132 data, and/or can transmit instructions to the CCM 130, such as to alter administration of treatment by the CCM 130.

The defibrillation device 140 can administer defibrillation therapy, such as electrical shocks, to the patient and can include a sensor(s) 142, such as for monitoring one or more physiological parameters of the patient. Additionally, or alternatively, the defibrillation device can receive patient physiological and/or other data from the optional sensor(s) 120. The defibrillation device 140 can transmit and/or receive information with the medical device 110. The information transmitted to the medical device 110 can include patient physiological information and/or patient treatment information, such as information regarding administered defibrillation therapies. The information received by the defibrillation device 140 can include the output, and/or instructions, from the medical device 110. The output, and/or the instructions, from the medical device 110 can alter patient monitoring and/or treatment by the defibrillation device 140. In an example, the medical device 110 can track the administration of defibrillation shocks to the patient and the resulting effects of the administered treatment. The output of the medical device 110 can be used by, and/or include instructions for, the defibrillation device 140 to provide an altered, or different, treatment to the patient based on the previous treatment and/or the physiological state trends of the patient.

The defibrillation device 140 can also communicate with the one or more remote locations 150. The communications can include sending and receiving of information and/or instructions. That is, the remote location 150 can receive data from the defibrillation device 140, such as sensor(s) 142 data, and/or can transmit instructions to the defibrillation device, such as to alter the administration of treatment by the defibrillation device 140.

The remote location 150 can communicate with the medical device 110 and/or other devices and/or systems that are used in monitoring and/or treating the patient. The medical device 110 and/or other devices and/or systems can receive data and/or instructions from the remote location and can provide data, such as patient physiological and/or treatment data, to the remote location 150. The remote location 150 can also provide additional patient information, such as previous treatment and/or monitoring history to other users, devices and/or systems, such as the medical device 110. The remote location 150 can be a user, device and/or system external from the medical device 110, such as a mobile computing device 152, a medical director 154, a remote server 156, an online medical control physician 158, and/or other external users, devices and/or systems.

The mobile computing device 152 can be a portable device, such as a tablet, that can be connected to the medical device 110 and/or other devices/systems, such as by an integrated patient monitoring and/or treatment network. The mobile computing device 152 can receive, and/or obtain, patient information, such as from the medical device 110, and can provide an interface for a user to interact with one or more of the connected devices and/or systems, such as the medical device 110. The user can interact with the mobile computing device 110 to evaluate the patient data, to provide instructions regarding patient treatment and/or monitoring and/or for other functions and/or features. Additionally, the mobile computing device 152, and/or other remote locations 150, can provide, or assist, with analysis of the patient data, such as physiological trend(s) analysis, that can be provided to the medical device 110 and/or other users, devices and/or systems.

The medical director 154 can be an administrator that can assist with patient monitoring and/or treatment decisions, such as on an individual patient level or on a more generalized patient treatment protocol level. The medical director 154 can provide information and/or input to the medical device 110 to assist with the output by the medical device 110. For example, the medical director 154 can provide, or set, triggers/limits regarding physiological parameters to cause certain treatment, or other, events to occur in response to specific, or ranges, of physiological parameter data. The provision or setting of triggers/limits by the medical director can occur prior to deploying the device, and prior to the patient treatment event in which the device will be used.

The online medical control physician 158 can be provided patient data by the system, allowing them to provide real-time guidance regarding patient treatment and/or monitoring. Communication between the online medical control physician 158 and a user of the medical device 110 and/or the other medical devices 130, 140 can allow the online medical control physician 158 to provide instructions for monitoring and/or treating the patient. Such communication can allow providers to better tailor the resuscitation process and decision-making to the evolving course and real-time status of the patient.

The remote server 156 can store and/or transmit received information, such as patient data, treatment protocol data and/or other data. One or more external users, devices and/or systems can transmit and/or receive such information from the remote server 156. Additionally, the remote server 156 can include the ability to analyze the received patient data for further analysis, such as trend analysis and/or other analysis, to further develop and/or refine patient treatment/ monitoring protocols. For example, the remoter server 156 can analyze the collected patient data to determine more effective patient treatment protocols that can be implemented based on patient physiological parameter data.

Figure 2:
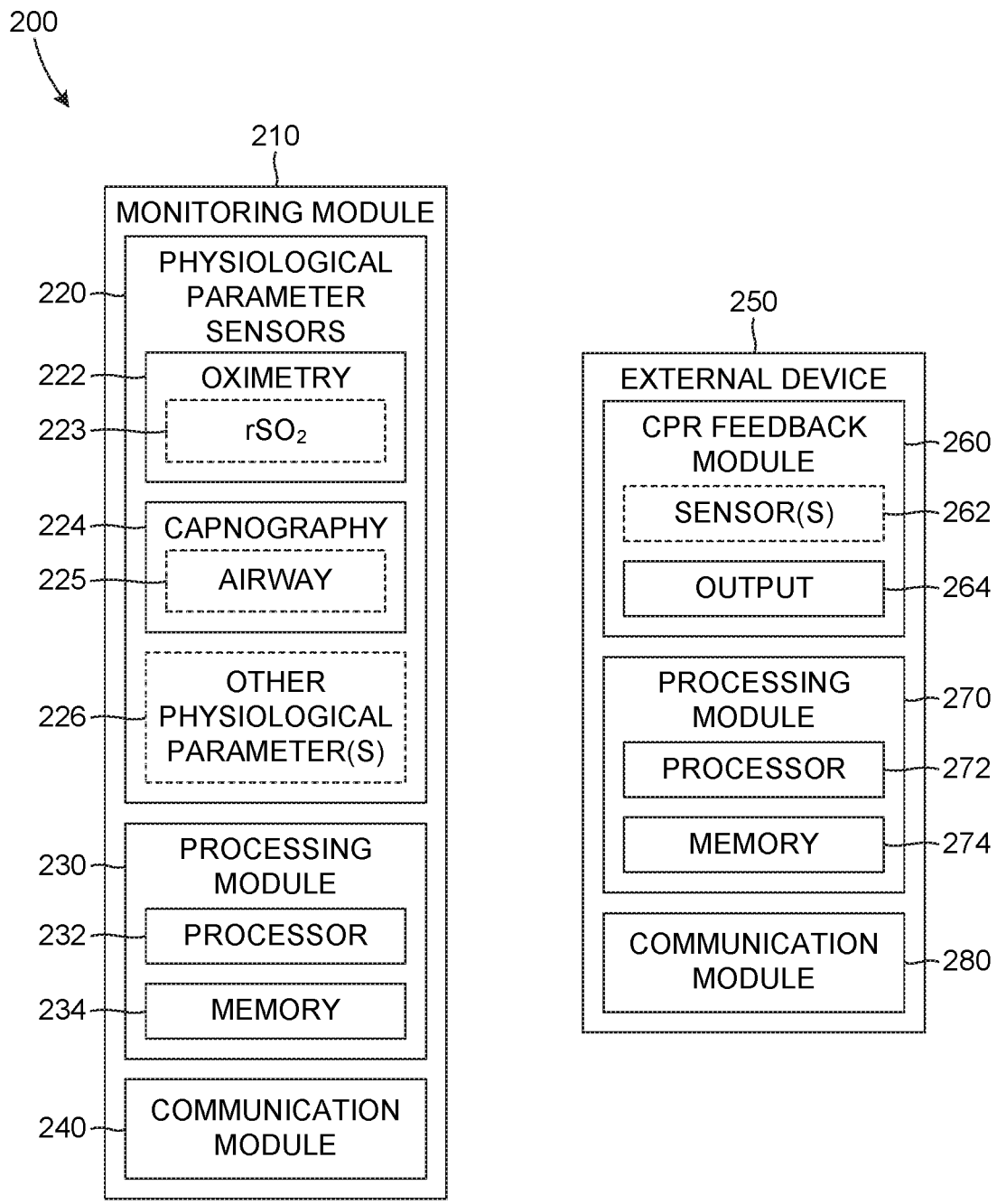
FIG. 2 is an example block diagram of another physiological feedback system.

FIG. 2 is an example physiological feedback system 200 that includes a monitoring module 210 and an external device 250. The external device 250 can monitor and/or treat a patient while in communication, or connected, with the monitoring module 210. The monitoring module 210 can sense and/or receive capnography and/or oximetry data of the patient to monitor and/or assess an aspect of the physiologic state of the patient. The monitoring module 210 and/or the external device 250 can use the physiologic state information to assess treatment efficacy, such as cardiopulmonary resuscitation (CPR) effectiveness. In response to the assessment, the monitoring module 210 and/or the external device 250 can advise, or instruct, on further treatment and/or modification, or alteration, of treatment being administered, such as CPR.

In addition to assessing CPR effectiveness, the physiologic state information of the patient can also be used to assess brain function based on the cerebral tissue oxygenation. During cardiac arrest, blood flow is ineffective and oxygen deprivation of various tissues results due to the lack of blood flow. CPR mechanically forces blood flow so that oxygen deprivation is slowed. Brain and nervous tissue is susceptible to damage due to oxygen deprivation, so cerebral tissue oxygenation information can also be used to assess the magnitude of oxygen deprivation in the brain. Trends in cerebral tissue oxygenation over time can also be used to assess the likelihood and/or magnitude of damage to the brain, and such information can in turn be used in decision-making regarding additional treatments and resuscitation efforts.

The monitoring module 210 can include physiological parameter sensors 220, a processing module 230 and a communication module 240. The physiological parameter sensors 220 can be connected to and/or communicate with the monitoring module 210. Alternatively, the sensor data can be provided to the monitoring module 210 from one or more external users, devices and/or systems. The physiological parameter sensors 220 can include one or more oximetry sensors 222, one or more capnography sensors 224, and one or more other physiological parameter(s) sensors 226, in some examples. The oximetry sensors 222 can provide sensor data regarding tissue and/or blood oxygenation levels of a patient which one or more oximetry sensors 222 are monitoring. The capnography sensors 224 can provide sensor data regarding the expired $CO_2$ levels of the patient. The other physiological parameter(s) sensors 226 can provide sensor data regarding other physiological parameters, such as ECG data, non-invasive blood pressure data, pulse oximetry data and/or other data regarding other physiological parameters.

The oximetry sensors 222 can include regional tissue oxygenation ($rSO_2$) sensors 223 that can be placed on the patient to monitor oxygenation of the tissues underneath the sensors 223. One or more of the $rSO_2$ sensors 223 can be placed on the patient's head, such as on the patient's forehead, to monitor cerebral tissue oxygenation, for example. The $rSO_2$ sensors 223 can be light-based sensors that include one or more light emitters and detectors. The light emitters of the $rSO_2$ sensors 223 can emit Near Infrared light having various light characteristics, such as one or more frequencies and/or wavelengths. The emission of Near Infrared light having multiple wavelengths can be used to sense oxygenation of blood at various depths beneath the $rSO_2$ sensor 223. Near Infra-Red Spectometry (NIRS) can be used to calculate the oxygenation level of the blood in tissues under the $rSO_2$ sensor 223. The NIRS processing can be performed by the monitoring module 210, and/or by an external device and/or system, to determine the blood/tissue oxygenation data. Additionally, the NIRS processing can provide a broad measure of blood oxygenation levels by providing oxygenation data that is a combination of venous and arterial blood oxygenations. The oximetry data, such as provided by the $rSO_2$ sensor 223 and processing of data therefrom, can provide a measure of the patient's oxygenation state and/or the balance between oxygenated and deoxygenated blood in the tissue being measured by the sensor.

The capnography sensors 224 measure fraction or partial pressure of $CO_2$ in gases in the airway, and from that airway $CO_2$ signal end-tidal $CO_2$ ($EtCO_2$) can be calculated. An airway $CO_2$ sensor 225 can monitor the $CO_2$ expelled from the patient which can provide an indication of the patient's $CO_2$ levels and, since blood flow is the primary means of transport of $CO_2$ from the lungs, an indication of the amount of blood flow occurring in the patient.

The processing module 230 can include a processor 232 and memory 234. The processor can analyze and/or evaluate data, such as received from the physiological parameter sensors 220 and/or the communication module 240, and/or control one or more functions and/or features of the monitoring module 210. The memory 234 can store data, such as received from the physiological parameter sensors 220 and/or the communication module 240, and/or instructions and/or processes for the processor 232 to perform.

The communication module 240 can communicate with external devices and/or systems, such as the external device 250, using one or more communication protocols and/or connections, such as Wi-Fi, the Internet, Bluetooth® and/or other protocols and/or connections. Data can be transmitted from and/or received to the tissue oxygenation module 210 via the communication module 210. For example, the communication module 240 can receive physiological parameter data and/or treatment data from the external device 250 and can transmit a tissue oxygenation value and/or treatment instructions to the external device 250.

The external device 250 can include a CPR feedback module 260, a processing module 270 and a communication module 280. The external device 250 can monitor the physiological state of the patient and/or monitor patient treatment and provide instructions for additional treatment and/or modification of the current patient treatment. Monitoring a patient's physiological state and/or treatment can include collecting physiological parameter data from the patient and/or data from the administration of treatment to the patient.

The CPR feedback module 260 can include a sensor(s) 262 to monitor one or more parameters of CPR administration, such as compression rate and/or depth, and an output 264. The sensor 262 can be connected to and/or in communication with the CPR feedback module 260, to provide data regarding one or more CPR parameters. Alternatively, the CPR parameter data can be supplied to the external device 250 by another device and/or system that generates CPR parameter data. The output 264 can provide information to a user regarding the administered CPR, such as feedback, including an assessment of the administered CPR and/or instructions to alter one or more parameters of the administered CPR. The output can communicate this information in a visual and/or audible format, such as by a display screen and/or a speaker. The user can interpret the provided visual and/or audible output 264 to initiate and/or modify treatment of the patient.

The processing module 270 includes a processor 272 and memory 274. The processor 272 can analyze and/or evaluate data, such as the tissue oxygenation value received from the tissue oxygenation module 210, and/or control one or more functions and/or features of the tissue external device 250. The memory 274 can store data, such as received from the CPR feedback module 260 and/or the communication module 280, and/or instructions and/or processes for the processor 274 to perform.

The communication module 280 can communicate with external devices and/or systems, such as the tissue oxygenation module 210, using one or more communication protocols and/or connections, such as Wi-Fi, the Internet, Bluetooth® and/or other protocols and/or connections. Data can be transmitted from and/or received to the external device 250 via the communication module 280. For example, the communication module 280 can receive tissue oxygenation data and/or treatment from the tissue oxygenation module 210 and can transmit CPR parameter data to the tissue oxygenation module 210.

In an embodiment, the monitoring module 210 can monitor tissue oxygenation levels of the patient using the oximetry sensor data 223, and/or levels of $CO_2$ expired by the patient using capnography sensor 224 data. From the collected oxygenation data, the monitoring module 210 can calculate a tissue oxygenation value. From the collected capnography data, the monitoring module can calculate $EtCO_2$, providing an indirect assessment of pulmonary blood flow. The external device 250 can collect CPR parameter data, such as compression depth and rate, and can transmit the collected CPR parameter data to the monitoring module 210. The monitoring module 210 can use the received CPR parameter data, and/or the calculated tissue oxygenation value, and/or the $EtCO_2$ level, to determine an effectiveness, or feedback, of the CPR being administered. In response to that determination, the monitoring module 210 can provide instructions to the external device 250 to cause the administrator of the CPR to alter one or more of the CPR parameters and/or can provide the CPR feedback data to the external device 250 for output 264 and/or CPR instruction/alteration determination and output. In this manner, CPR effectiveness can be determined based on tissue oxygenation data, and/or airway $CO_2$ data, and one or more parameters of CPR administration can be altered in response to, and/or based on, the tissue oxygenation data. Alteration of the CPR administration can be done to increase or redirect blood flow and thereby assist with increasing tissue oxygenation levels which can assist with preventing damage, such as due to hypoxia, and/or can improve the probability of achieving ROSC. In a further, or alternate, embodiment, the external device 250 can be a mechanical CPR device, such as a chest compression machine (CCM), and the operation of the mechanical CPR device can be automatically altered, or altered at the discretion of the rescuer, based on the tissue oxygenation data and/or the airway $CO_2$ data.

While the monitoring module 210 and the external device 250, such as a defibrillator, patient monitor, monitor/defibrillator, mechanical CPR device and/or other medical treatment and/or monitoring device, are shown as separate elements, one or more features and/or functionality of one or more of the tissue oxygenation module 210 and the external device 250 can be combined and/or integrated with the other and/or another device.

Figure 3:
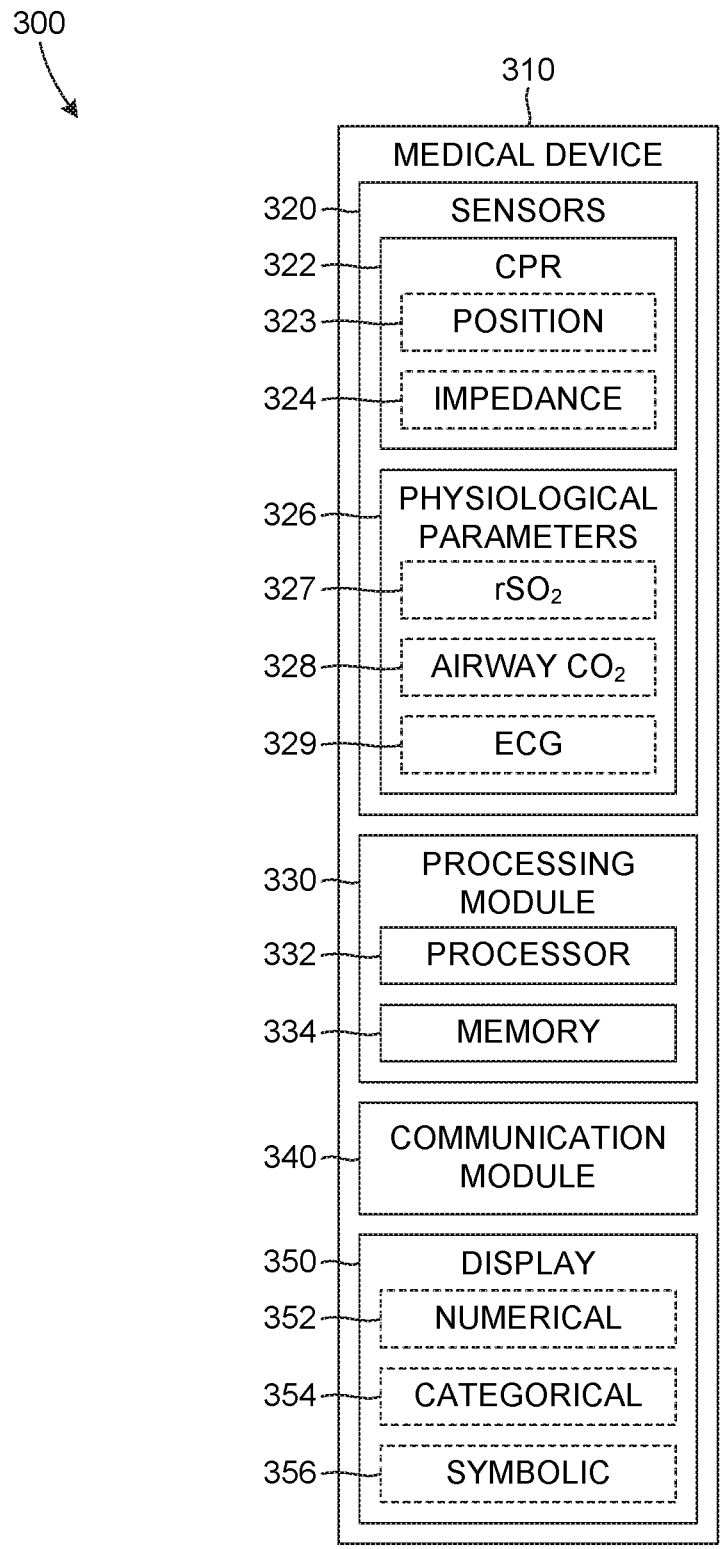
FIG. 3 is an example block diagram of a further physiological feedback system.

FIG. 3 is an example physiological feedback system 300 that includes a medical device 310. The medical device 310 can include one or more sensors 320, a processing module 330, a communication module 340 and a display 350. The one or more sensors 320 can be coupled to a patient to receive/sense data regarding the patient, such as one or more physiological characteristics/parameters of the patient. Alternatively, or additionally, the medical device 310 can receive data regarding the patient, such as physiological parameter data, from an external device, system and/or user. The medical device 310 can analyze, process and/or evaluate the sensed/received data to provide physiological feedback regarding the patient, such as treatment metrics and/or other feedback to guide treatment and/or monitoring of the patient.

Additionally, the medical device 310 can include input(s) regarding one or more confounders that can obscure patient physiological data and/or influence patient monitoring/treatment. The confounder data can be supplied to the medical device 31 via the communication module 340 and/or other inputs, such as by the sensors 320. Example confounders can include the administration of medications, administration of treatments, rescuer observations/inputs, and/or other inputs. The confounders, such as medication/treatment administration, can cause temporary changes in the physiological data of the patient that might obscure the patient's actual physiological state and/or trend thereof. Confounders, such as rescuer observations/inputs, can alter weighting/importance of one or more physiological parameters due to the observation/input. For example, a patient may exhibit signs of consciousness while in cardiac arrest and receiving CPR, which is uncommon but can indicate that cerebral blood flow and cerebral tissue oxygenation are high enough to support a degree of consciousness. Typically, the assessment of a patient in cardiac arrest assumes the patient is unconscious, so the observation of consciousness during such an event can be input to provide additional information that can be considered when assessing the patient, when interpreting other data from the resuscitation event, and/or when determining further patient monitoring/treatment.

The sensor(s) 320 can be placed on, or near, the patient and connected to, or in communication with, the medical device 310 to provide sensor data indicative of one or more physiological parameters of the patient, a physiological condition of the patient, treatment administered to the patient and/or other data regarding the patient. In the example of FIG. 3, the sensors 320 include one or more cardiopulmonary resuscitation (CPR) sensors 322 and/or one or more physiological parameter sensors 326. The CPR sensors 322 can provide data regarding the administration of CPR, or lack thereof. The data can include measurements of one or more CPR variables, characteristics of the CPR administration and/or other data regarding the administration of CPR. The physiological parameter sensors 326 can provide data regarding one or more physiological parameters of the patient.

The CPR sensors 322 can be placed on and/or near the patient and can include a position sensor 323, an impedance sensor 324 and/or other sensors to measure, monitor and/or assess the administration of CPR to a patient. The position sensor 323 can include one or more elements that are placed on the patient to which CPR is being administered, on the person of a user administering CPR to the patient, and/or placed proximal the patient, such as above the patient, on a surface near the patient, beneath the patient and/or other patient adjacent locations. One or more signals can be generated by the position sensor 323 that can be indicative of one or more parameters/characteristics of the administered CPR, such as a rate of compressions, the depth of compressions, the number of compressions and/or other parameters/characteristics related to the administration of CPR to the patient. The impedance sensor 324 can measure a transthoracic impedance of the patient, such as by a pair of electrodes placed on the patient, and the measured data can be indicative of CPR administration since the transthoracic impedance of the patient changes in response to administered compressions.

The physiological parameter sensors 326 can include a regional tissue oximetry ($rSO_2$) sensor 327, such as to measure cerebral tissue oximetry, an airway $CO_2$ sensor 328, from which end-tidal $CO_2$ ($EtCO_2$) can be calculated, an electrocardiogram (ECG) sensor 329 and/or other physiological parameter sensors. The sensor signals generated by the $rSO_2$ sensor 327 and/or the airway $CO_2$ sensor 328 can be indicative of the level of blood flow in the patient. Such data can be used to assess and/or analyze the physiological state of the patient. Additionally, such physiological parameter data can provide information regarding potential future patient physiological states, provide information for treatments and/or interventions, and/or other information for use in monitoring and/or treating the patient. Further, the collected physiologic and/or patient data can be used for pattern, and/or other, analysis to aid in developing and/or refining the plan for ongoing patient treatment, monitoring and/or assessment.

The ECG sensor 329 can include two or more electrodes that are placed on the patient and provide sensed data to the medical device 310.

Reception of sensed data, from the sensors 320, by the medical device 310 can be via wired and/or wireless connection(s). In an embodiment in which the transmission of data is via a wireless connection, the sensed data and/or the connection can be encrypted/secured to protect the integrity of the transmitted sensor data. Additionally, the sensed data can be communicated to the medical device 310 from one or more other devices and/or systems that monitor/sense physiological parameter data of the patient.

The processing module 330 can include a processor 332 and memory 334. The processing module 330 can control one or more functions and/or features of the medical device 310. Additionally, the processing module can receive various data/information, such as from the sensors 320 and/or a user, device and/or system, for collection and/or analysis. The collection and/or analysis of data by the processing module 330 can assist with patient assessment, treatment and/or monitoring. Further, such data can also be processed for multiple patients to determine trends and/or patterns that can assist with future patient assessment, monitoring and/or treatment. The processing module 330 can also collect and store information regarding patient instances, such as assessment, monitoring and/or treatment data, that can be transmitted, or provided, to a user, device and/or system upon conclusion of the patient instance.

The communication module 340 can transmit and/or receive information from/to the medical device 310 and one or more external devices and/or systems. The communication module 340 can communicate with the one or more external devices and/or systems via one or more communication protocols and/or connections, such as Bluetooth®, Wi-Fi, the Internet and/or other communication protocols and/or connections. Communications to and/or from the communication module 340 can be via a secure communication channel and/or can be encrypted, to preserve the integrity, or security, of the communications. In an example, one or more of the sensors 320 can be part of an external device/system that transmits sensed data to the medical device 310 via the communication module 340.

The display 350 can provide information in a visual format to a user, device and/or system. To provide the information, the display 350 can include one or more screens, lights and/or other visual indicators, to display, or provide, information in a visual format. The display 350, or portion thereof, can also be configurable allowing the format and/or other characteristics of the display to be altered, such as in response to the user and/or by the processing module 330. The configurability of the display 350, or portion thereof, can allow the display 350 to provide relevant information in a more accessible manner, such as by highlighting priority information more than other information displayed by the display 350.

Example visual formats the display 350, or portion thereof, can display information in a numerical format 352, a categorical format 354 and/or a symbolic format 356. The numerical format 352 can include displaying numerical values, such as measurements of physiological parameters, on the display 350. The categorical format 354 can include displaying and/or highlighting a category, such as a negative, neutral and/or positive category for a variable like a physiological parameter. The categorical format 354 can also be represented by one or more colors that can change depending on the value of the category. For example, the color green associated with a category can indicate a positive and similarly, yellow can indicate neutral and red can indicate negative. Additionally, or alternatively, the categories of the categorical format can be displayed as variable indicators, such as a changing bar that can move or expand based on the measurement/value of the category. The variable indicator can also include color associations, such as those previously discussed. The symbolic format 356 can include graphical and/or textual representations of data, such as a text message and/or a graph. The format(s) of the display 350 are presented to aid in the speed and accuracy of determining the information represented, or displayed, thereon. Further, the display 350 can alter the format of information displayed based on the importance of the information. For example, information that is of lesser importance can be represented categorically 354, such as to reduce the necessary area required for the display of such information, the display format can change if the information becomes more relevant or important, such as to a numerical 354 and/or larger format to highlight the importance of the information and/or that the importance of such information has changed from a previous state. Again, such functionality assists with presenting the relevant information in a format that assists with the efficient and accuracy determination of the displayed information.

Figure 4:
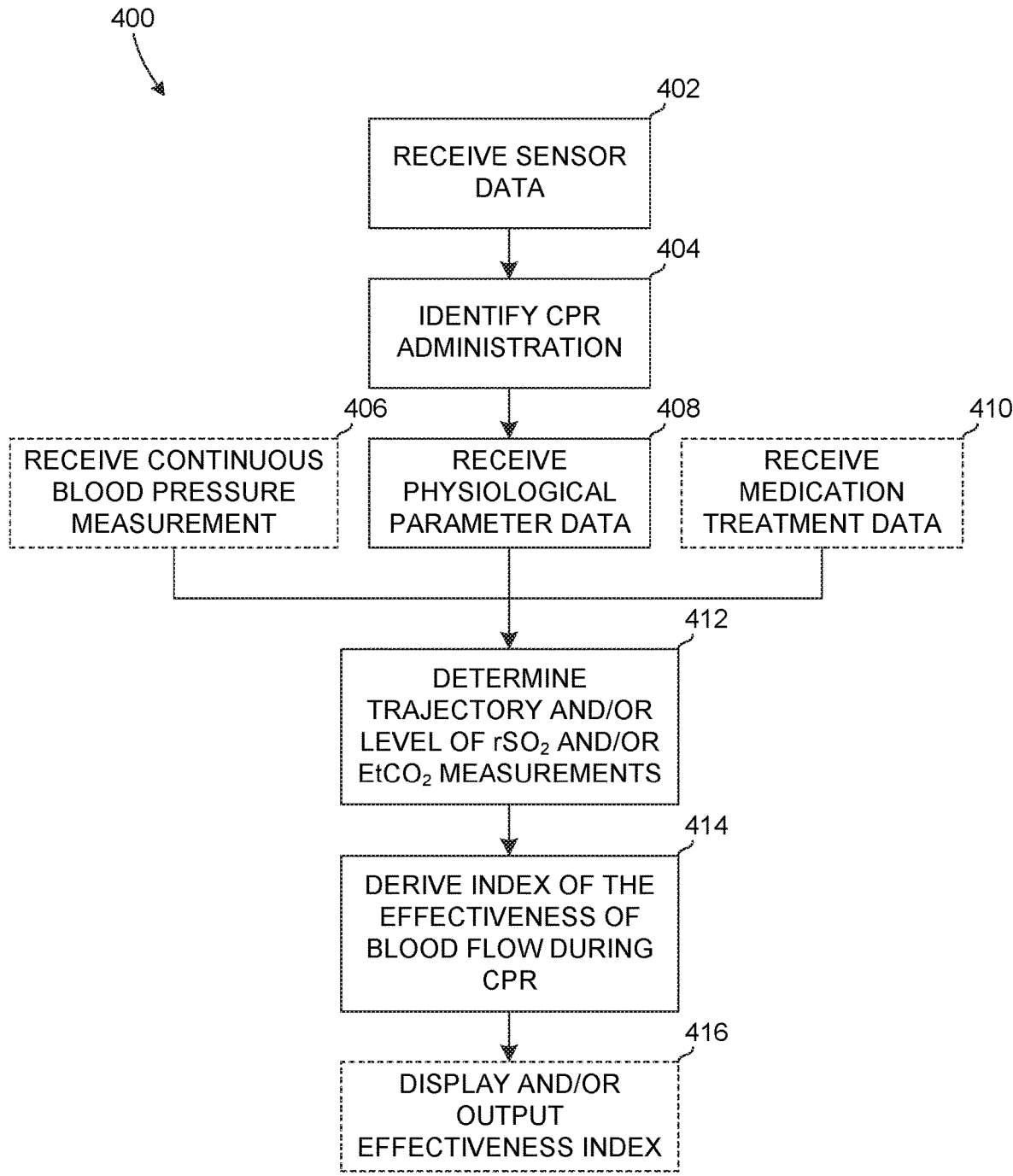
FIG. 4 is an example physiological feedback method.

FIG. 4 is an example physiological feedback method 400. At 402, sensor data is received. In an example, the sensor data can include data regarding physiological parameters of a patient, such as regarding their end-tidal $CO_2$ levels, their tissue oximetry levels, and/or their heart rhythm assessed from the sensed ECG data, and/or data regarding CPR administration, such as transthoracic impedance and/or CPR positional data. At 404, CPR administration can be identified in the received sensor data, such as at 402. Identification of CPR administration can be determined from various sensor data, such as transthoracic impedance data and/or CPR sensor data. The identification of CPR administration, such as at 404, can include identifying the onset, or beginning, of CPR administration and/or one or more characteristics of the administered CPR, such as a rate of compressions, a depth of compressions and/or other characteristics.

At 406, optionally, continuous blood pressure measurement data can be received. The continuous blood pressure measurement data can be collected using a non-invasive and/or an invasive system/method of obtaining blood pressure measurement data. The collected blood pressure data can include an arterial diastolic blood pressure and/or other blood pressure measurements. The blood pressure measurement data can be received from a user, device and/or system.

At 410, optionally, medication treatment data can be received. Medication treatment data can include identification of medications administered to the patient and can also include additional information regarding the medication, such as a dosage, manner of administration, time of administration and/or other information/data regarding the medication and/or its administration. The medication treatment data can be received from a user, device and/or system. For example, certain medications, such as sodium bicarbonate, that are typically administered in response to cardiac arrest can cause temporary changes in one or more physiological parameters, such as $EtCO_2$ in the example of sodium bicarbonate. The increased $EtCO_2$ due to the sodium bicarbonate administration could be incorrectly assumed to be due to increased blood flow in the patient, however, by providing medication data, the process 400 can account for this temporary increase in $EtCO_2$. This accounting can be done by comparing the increase in the $EtCO_2$ to other physiological parameter data, such as oximetry data, to determine if a commensurate effect is also observed that would be indicative of a physiological state change in the patient, rather than a change due to a confounder, such as the medication administration. Similarly, other patient treatments, such as intubation, can cause confounding effects that the process 400 can account for and/or consider in deriving the index. Additionally, the process 400 can account for other confounders, such as environmental and/or contextual confounders, that can be input to the process 400, such as by a user, device and/or system.

At 408, physiological parameter data can be received. The received physiological parameter data can include capnography data, such as $EtCO_2$ data/measurements, and also can include $rSO_2$ data. Other and/or additional physiological parameter data can also be received, such as ECG data. At 412, a trajectory and/or level of $rSO_2$ and $EtCO_2$ measurements can be determined. Determination of the trajectory of the $rSO_2$ and $EtCO_2$ measurements can include analyzing/evaluating the received physiological parameter data, such as from 408. Based on the analysis/evaluation, a trajectory for one or both the $rSO_2$ and $EtCO_2$ measurement data can be determined, such as a downward, or declining, or an upward, or improving, trajectory. Such trajectory information can be indicative of a patient's improving, stable, or declining physiological condition. The levels of $rSO_2$ and/or $EtCO_2$ can be expressed as percentages and/or other forms. Similar to the trajectory, the level information can be indicative of the patient's improving, stable, or declining physiological condition. Additionally, the trajectory and/or levels of the $rSO_2$ and $EtCO_2$ measurements provide an indication of the patient's current physiological condition. Such information can be used to assess the current treatment the patient may be receiving and/or if changes should be made to the treatment.

At 414, using the trajectory and/or level data of 412, an index of the effectiveness of treatment, such as blood flow during CPR administration to the patient, can be derived. This effectiveness index provides information regarding the patient's physiological response to the administered CPR. Using the effectiveness index, the administration of CPR can be evaluated to determine if changes to the administration of the CPR should be made. At 416, the derived effectiveness index can be displayed, such as on a display of a medical device. A user, such as the user administering CPR, can review the derived index to modify or alter the administration of CPR. Alternatively, and/or additionally, CPR administration modifications and/or alterations can also be displayed with the derived index. The displayed modifications and/or alterations can be based on the received data, such as at 402, 406, 408 and/or 410, and can include modification and/or alteration of one or more of the characteristics of the administered CPR. Additionally, the modifications and/or alterations can include other intervention instructions, or suggestions, such as the administration of medications and/or other treatments.

The derived effectiveness index can be continuously modified and/or updated based on received data, such as physiological parameter data. In an example, CPR parameter measurement data, such as compression rate, compression depth, compression recoil adequacy, ventilation rate, ventilation tidal volume and/or other CPR parameter(s), or characteristic(s), measurement data, can be received in substantially real-time. The real-time acquisition of such data allows the received CPR parameter measurement data to be correlated to other received data and the derived effectiveness index can be updated and/or modified based on the correlated data. The correlation of the data can allow determinations regarding changes in the CPR administration and their effect on other measured physiological parameter data, such as the $rSO_2$ and/or $EtCO_2$.

Administered medications can also affect the received physiological parameter data. The received medication treatment data of 410 can be correlated to the received physiological data and the derived effectiveness index can be updated and/or modified based on the correlated data. For example, administration of a medication can cause improvement in one or more of the $rSO_2$ and/or $EtCO_2$ measurements. Correlation of medication administration to the improvement in the physiological parameter measurement data can allow the derived effectiveness index to indicate that such improvement is possibly temporary or possibly greater improvement that an actual improvement in the physiological condition, or state, of the patient. In addition to administered medications, the derived effectiveness index can also be updated and/or modified based on treatment administration, such as an intubation of the patient. The treatment administration can also be correlated with other physiological parameter measurements and the derived effectiveness index can be updated and/or modified based on such correlated data. The correlation of administration of treatments and/or medications with physiological data changes can assist with identifying, and/or removing, confounders and their effects from the derived effectiveness index. The derived effectiveness index is therefore more representative of the physiological state of the patient and/or trends thereof.

The correlation of events, such as medication administration, changes to the CPR administration and/or treatment administration, to the physiological parameter measurement data can allow the derived effectiveness index to more accurately, or more truly, represent the effectiveness of blood flow, or a physiological state, of a patient during CPR administration. The derived effectiveness index including such correlation information can be more useful in determining further treatment of the patient, since more accurate assessments of the patient's physiological condition can be made by a user, device and/or system.

The derived effectiveness index can be displayed at 416 in one or more formats, such as a numerical, categorical and/or symbolic format. As a numerical format, the derived effectiveness index can be displayed as a value, such as from 0-10. As a categorical format, the derived effectiveness index can be displayed as a categorical value, such as "worsening," "stable," or "improving." As a symbolic format, the derived effectiveness index can be displayed as a pictograph and/or textual message.

In an example in which the received data is indeterminate and/or unable to be accurately correlated, the derived effectiveness index may not be displayed. Rather than displaying the derived effectiveness index, a notification can be displayed to indicate the derived effectiveness index is indeterminate. Typically, when the derived effectiveness index is indeterminate, often the physiological state of the patient is improving in response to the administered treatment and that is why the process 400 is unable to accurately correlate the administration of treatment and/or its effects. In an example, an indeterminate indication can be accompanied by instructions to continue the current treatment until the derived effectiveness index is no longer indeterminate and an assessment of the patient can be made. Once the derived effectiveness index is no longer indeterminate, the display can remove the indeterminate notification and can display the derived effectiveness index.

Figure 5:
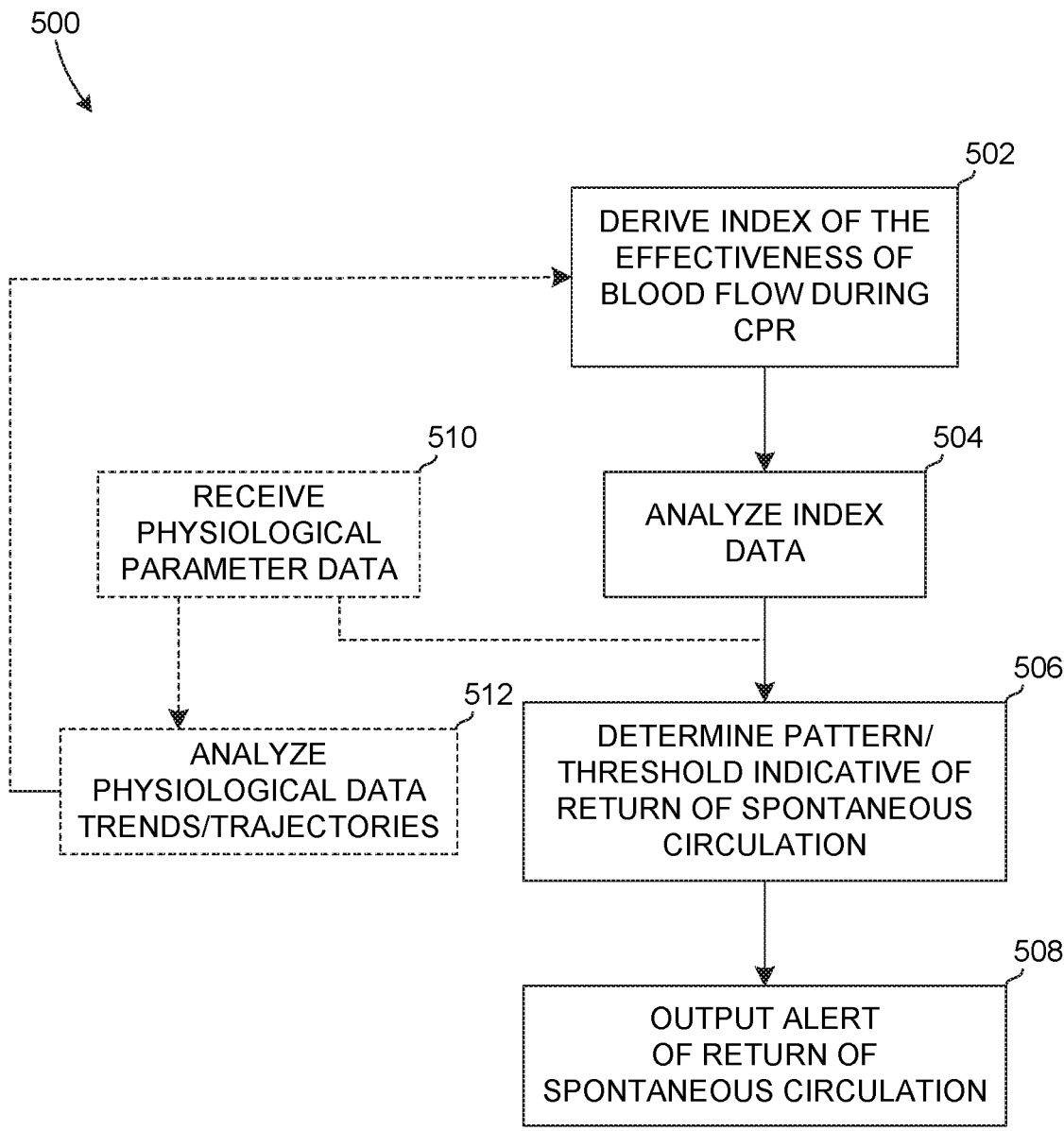
FIG. 5 is a further example physiological feedback method.

FIG. 5 is an example physiological feedback method 500. The physiological feedback method 500 can provide determination of indications of Return of Spontaneous Circulation (ROSC) in a patient. CPR administration to a patient can be altered, and/or discontinued, based on a determination of ROSC. The continued administration of CPR to a patient having ROSC can induce fibrillation in the patient, and/or otherwise contribute to the patient deteriorating back into cardiac arrest. As such, the determination of ROSC is important factor in monitoring and/or treating the patient, such as the determination to transport the patient to a hospital or other healthcare facility.

At 502, an index of the effectiveness of blood flow during CPR can be derived, such as by the method 300 of FIG. 4. At 504, the index data can be analyzed and at 506 patterns and/or thresholds indicative of ROSC can be determined from the index data. In addition to the index data, the determination of patterns/thresholds indicative of ROSC can, optionally, also be based on received physiological parameter data at 510. The received physiological parameter data can include an ECG signal. The ECG signal can be filtered to remove CPR induced artifacts. The optional physiological parameter data and the index data can be evaluated for patterns and/or thresholds indicating that the patient may have ROSC. If such a determination is made, an alert can be output at 508. The output can be an audible and/or visual notification to a user, such as a CPR administrator, that ROSC may have occurred in the patient.

In addition to optionally receiving physiological parameter data at 510, the method 500 can also optionally include analyzing the physiological parameter data for trends and/or trajectories at 512. The trend/trajectory information can be used to further refine, update and/or modify the index at 502. In this manner, the patient can be continuously and/or regularly assessed for potential ROSC.

In an example, the physiological parameter data can include an ECG signal and the measurements and/or trajectories of the patient's heart rate and/or QRS complex morphology can also be used to derive the index at 502. Further, a transthoracic impedance signal can also be included in the received physiological parameter data. Measurements and/or trends of the transthoracic impedance signal, and/or QRS-synchronous features contained therein, can be used to derive the index at 502. One or both of the ECG and transthoracic impedance signal can be used to derive the index and assist with determination of potential ROSC in the patient. If an invasive arterial pressure signal is available, this signal can be used by itself or in combination with other physiological signals to derive the index. In particular, presence of blood pressure pulses not correlated with chest compressions indicates a high, or increased, likelihood of ROSC.

Figure 6:
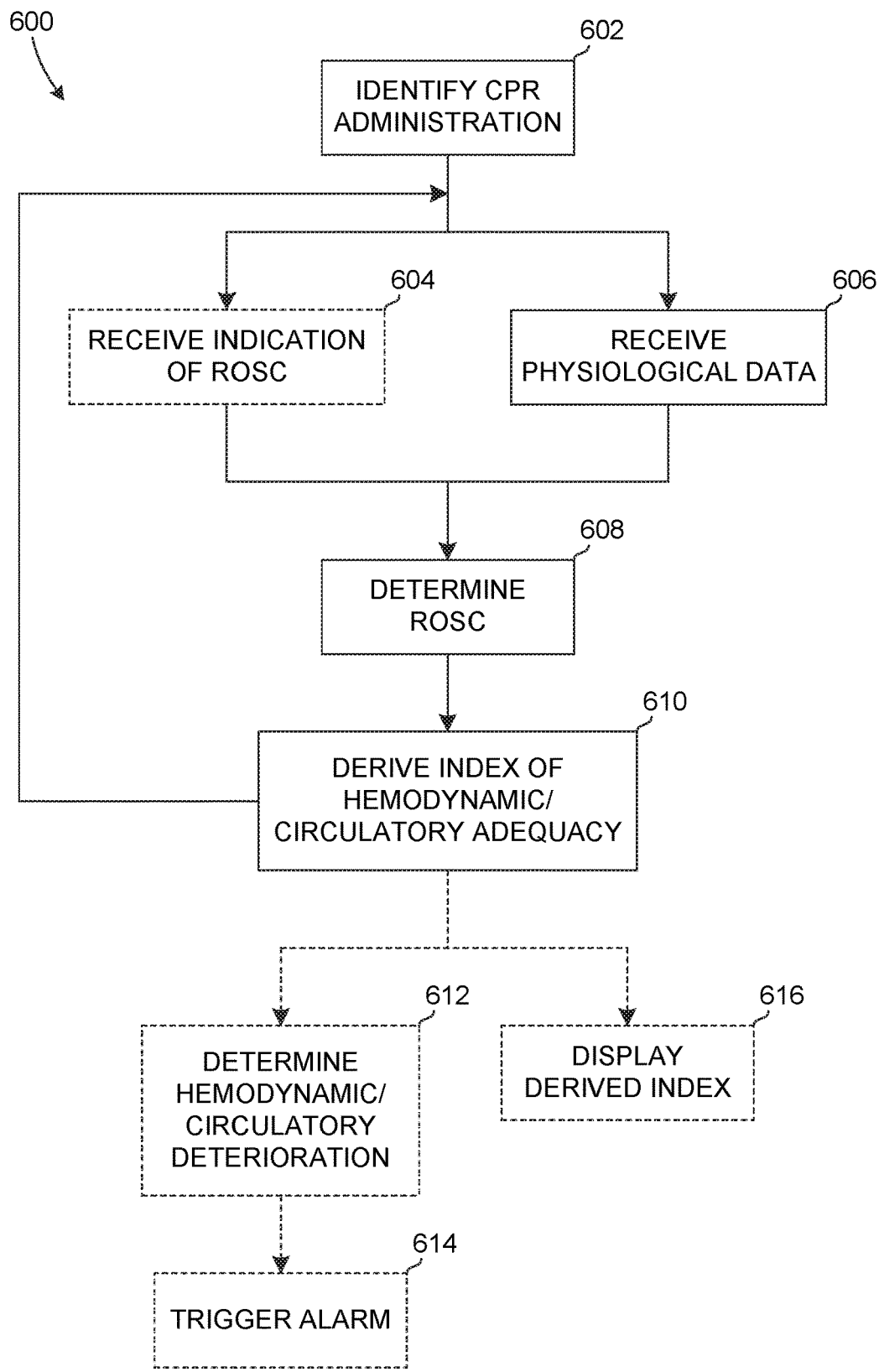
FIG. 6 is another example physiological feedback method.

FIG. 6 is an example physiological feedback method 600 that derives an index suggestive and/or indicative of hemodynamic and/or circulatory adequacy. At 602, CPR administration is identified, such as by one or more CPR and/or transthoracic impedance sensors, as having been performed and is now not being performed. At 608, a determination that the patient has achieved ROSC is made. The determination at 608 can be based on a received indication of ROSC at 604, such as by a user input and/or based on received physiological data at 606. The user input can be through a device performing the method 600 and/or from an external device/system coupled to a device performing the method 600. At 610, an index suggestive and/or indicative of the hemodynamic and/or circulatory adequacy of the patient can be derived. The index can be derived from physiological data received at 606. The received physiological data can include $rSO_2$ and $EtCO_2$ measurement data from which levels and/or trajectories can be determined. The determined levels and/or trajectories of the $rSO_2$ and $EtCO_2$ data can be used to derive the index at 610. The process 600 can be iterative and/or repeated, with the derived index being updated and/or modified as further physiological and/or other data is received.

At 616, the derived index can be optionally displayed until CPR is resumed. The derived index can be displayed as a numerical value, such as a value on a range of values; a categorical value, such as "stable," "declining," or "improving;" and/or as a symbolic value, such as a textual and/or pictorial notification.

At 612, an optional determination of hemodynamic and/or circulatory deterioration can be made. The determination can be made based on the derived index of 610 and/or based on levels/trajectories of the $rSO_2$ and $EtCO_2$ measurements. A specific point and/or magnitude of the deterioration can be indicative of potential, or occurring, re-arrest in the patient.

At 614, an optional alarm can be triggered based on hemodynamic deterioration. Hemodynamic deterioration can include the decrease in blood flow through the patient, a decrease in tissue oxygenation and/or a decrease in other hemodynamic parameters/characteristics. Such deterioration can be an indication that a physiological state of the patient is potentially about to decline and/or that intervention is recommended, and/or required, to prevent and/or reduce the hemodynamic deterioration. The alarm can be based on one or more thresholds and can be escalating based on the one or more thresholds. The thresholds can be predetermined, user provided and/or a combination thereof. Additionally, the alarm can be indicative of the degree of hemodynamic deterioration detected and/or determined. In response to the alarm, a user monitoring and/or treating the patient can provide intervention, if needed.

Figure 7:
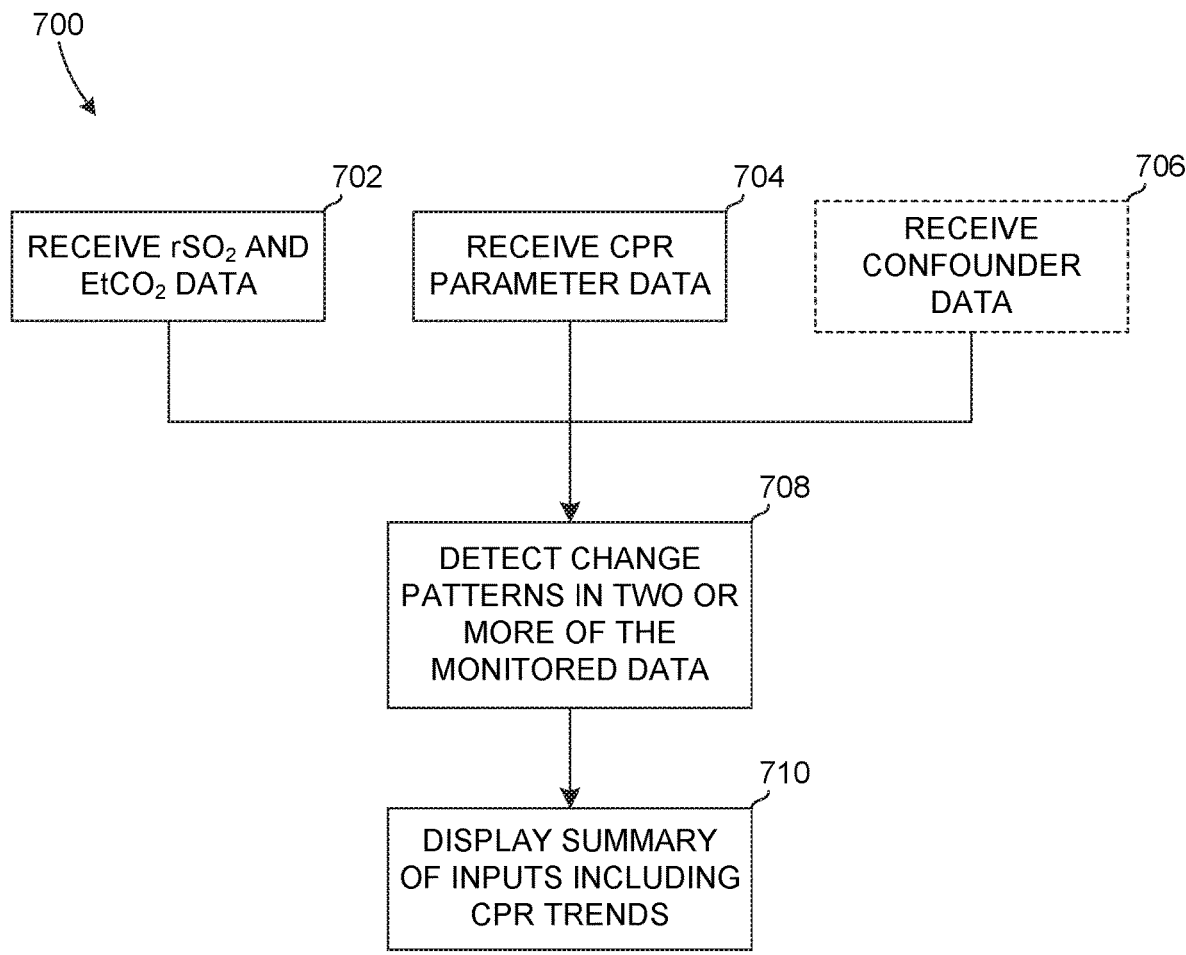
FIG. 7 is yet another example physiological feedback method.

FIG. 7 is an example physiological feedback method 700 that provides a summary of inputs that triggered a pattern detection to assist with identification of a cause, such as a confounder, and/or consequences of a change in one or more physiological parameters of a patient, such as a change in the physiological state, or trend, of the patient. At 702, $rSO_2$ and $EtCO_2$ data is received and at 704 CPR parameter data, such as compression rate and depth, is received. The received $rSO_2$ data can include tissue oxygen saturation information and can also include other information, such as tissue hemoglobin concentration, tissue blood volume index information, and/or similar information. At 706, optionally, confounder data, such as medication data, including identification, dosage, administration time and/or administration method, can be received. The confounder data input is environmental, contextual and/or medication data that can have a temporary, observable and/or detectable, effect of the patient's physiological state. Input of such confounder data allows the process 700 to account for these temporary effects so that the feedback provided is more indicative of the actual physiological state of the patient and/or trends thereof. At 708, change patterns in two or more of the monitored data, such as received at 702, 704 and/or 706, can be detected. The detection can be based on correlating pre-configured/predetermined change patterns with changes in the received two or more monitored data, such as the $rSO_2$ and $EtCO_2$ signals. The pre-configured change patterns can include a rate of change and/or other time-variant characteristics that can be correlated with the received physiological and/or other patient data. Optionally, the pre-configured and/or pre-determined change patterns can be user configurable, allowing a user or other to specify the change patterns to trigger detection of changes in the received data.

At 710, the summary of inputs, such as the inputs that triggered the pattern detection/correlation, and CPR trends can be displayed. For example, concurrent declines in the $rSO_2$ and $EtCO_2$ can trigger change pattern detection. In response, the $rSO_2$ and $EtCO_2$ data can be displayed. The displayed data can optionally include highlighting and/or other notification of the change pattern. Also displayed can be CPR trend data, such as changes in compression rate, depth and/or other CPR parameters. The concurrent display of such information can allow for a cause-and-effect determination. That is, it can be determined if treatment, such as CPR and/or medication administration, is responsible, or caused, changes in the physiological parameter data and/or the physiological parameter consequences dye to the change in treatment. A user monitoring and/or treating the patient can review the displayed summary to determine further changes to the treatment of the patient. Alternatively, evaluation of the summary can be performed by a device and/or system, and instructions and/or suggestions for/regarding the patient treatment can be provided.

The summary 710 can be displayed as a popup, or overlay, on a medical device, such as a monitor and/or defibrillator, being used to monitor and/or treat the patient. Alternatively, the summary can be provided on a device that is in communication with the treatment and/or monitoring device/system coupled to the patient. Example devices can include tablets and/or other computing devices communicating with the patient treatment/monitoring device/system via a patient care reporting and/or event recording system/software. The summary can be temporarily or continuously displayed and can also be configurable by a user to alter one or more characteristics of the display.

Figure 8:
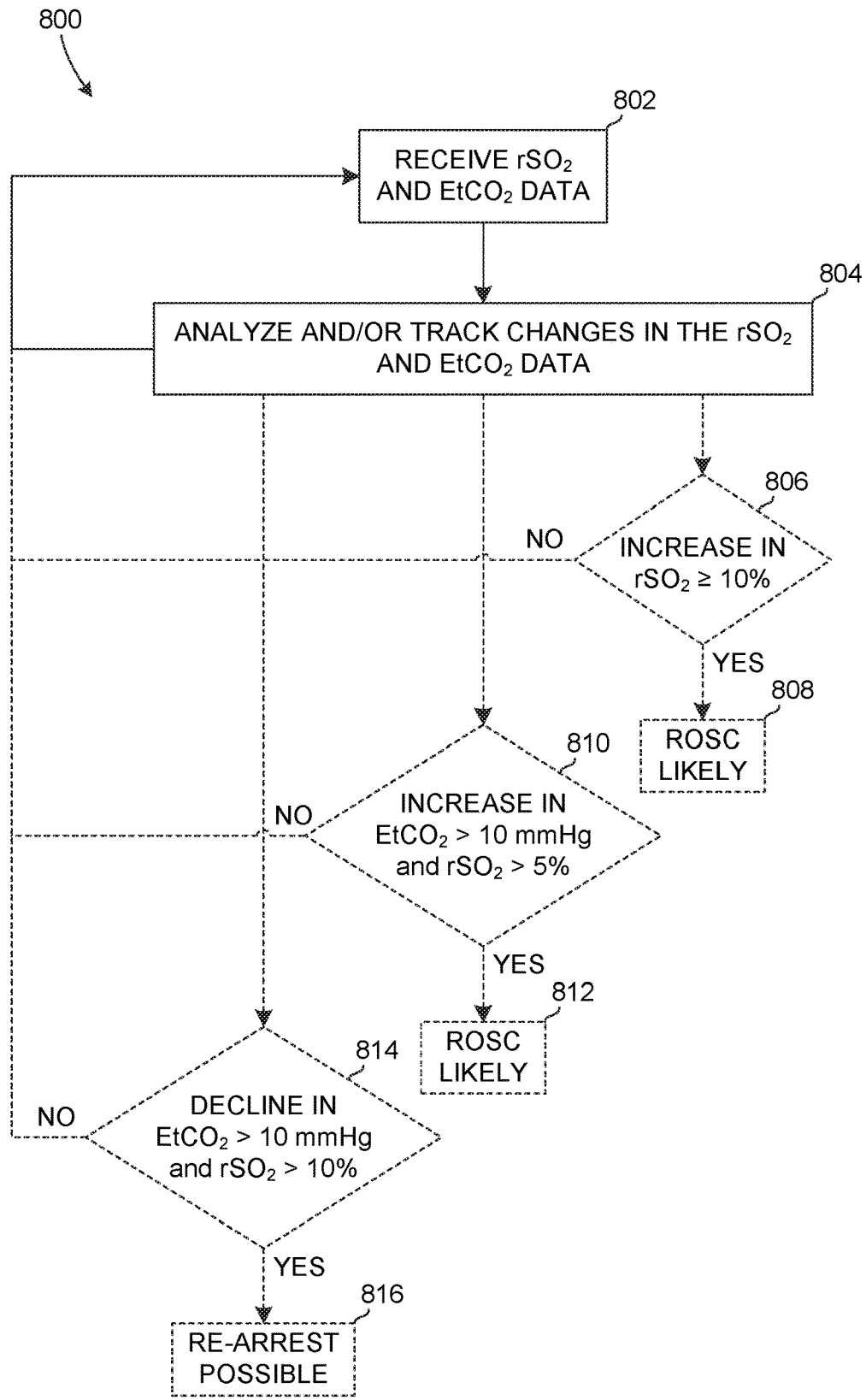
FIG. 8 is an example method of detecting the presence of Return of Spontaneous Circulation (ROSC).

FIG. 8 is an example method 800 for detecting ROSC. At 802, $rSO_2$ and $EtCO_2$ data can be received and at 804, the received data can be analyzed and/or changes in the data can be tracked. Based on the analysis and/or tracked changes, various indications of ROSC can be made. At 806, based on the analysis and/or change data, an increase of, for example, 10% or greater in the $rSO_2$ of the patient in a minute or less can be indication that ROSC is likely at 808. If no such change is detected and/or determined, the process 800 can return to receiving further capnography and/or tissue oximetry data for further analysis and tracking. At 810, an increase, within a short time period, in the patient's $EtCO_2$ of greater than, for example, 10 mmHg combined with an increase of, for example, greater than 5% in the patient's $rSO_2$ can be indicative of likely ROSC at 812. If no such changes are detected and/or determined, the process 800 can return to receiving further capnography and/or tissue oximetry data for further analysis and tracking. At 814, a sudden decline in $EtCO_2$ of, for example, more than 10 mmHg and a decline of greater than, for example, 10% in $sRO_2$ can indicate that the patient's return to a state of cardiac arrest, or re-arrest, is possible at 816. Threshold values, such as values higher or lower than those provided in these examples, may be implemented in the system, and may also be able to be configured by a user of the system. The possible re-arrest indication can provide a warning to allow treatment to be altered to prevent and/or prepare for the potential re-arrest of the patient. If no such changes are detected and/or determined, the process 800 can return to receiving further capnography and/or tissue oximetry data for further analysis and tracking. The repeated reception and analysis of capnography and/or tissue oximetry data can assist with the detection of future physiological states of the patient, such as the patient experiencing a likely ROSC and/or a possible re-arrest. The predictive notifications can allow for altered patient monitoring and/or treatment based on the notification.

Additionally, the process 800 can include input, by a user, device and/or system, of patient observations. In an embodiment, the input observations can alter one or more of the thresholds and/or decisions of the process 800. For example, a rescuer can input that a patient is exhibiting signs of consciousness during a cardiac arrest resuscitation effort. Additionally, other supplied inputs or observations can be assessed for their impact on potential rearrest and/or ROSC of the patient and can alter one or more of the decisions and/or thresholds of the process 800.

Figure 9:
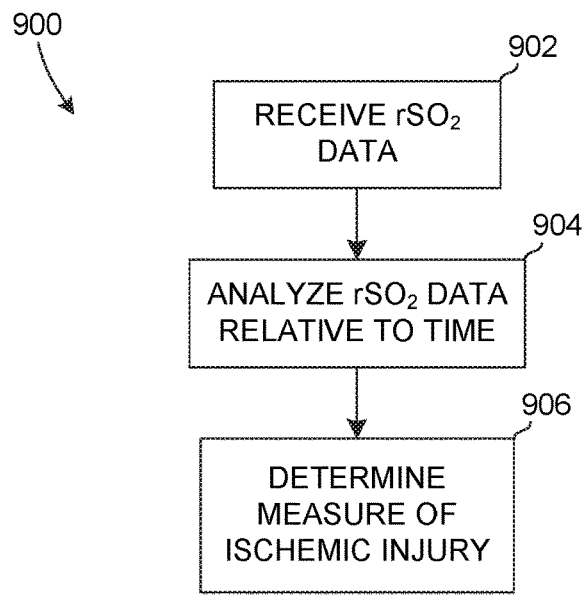
FIG. 9 is another example physiological feedback method.

FIG. 9 is an example method 900 of determining a measure, such as a magnitude, of an ischemic injury to a brain. Ischemic injury to the brain is caused by the brain being deprived of oxygen, such as can be experienced during a cardiac arrest. The measure of ischemic injury to the brain of a patient can be used in making treatment decisions regarding the patient. In an embodiment, a patient in cardiac arrest can experience brain hypoxia that causes ischemic injury to the brain. The ischemic injury can be assessed and/or quantified using the method 900 and further treatment decisions can be made. For example, for patients who remain in cardiac arrest for a prolonged interval, but in whom the determined aggregate ischemic exposure, or ischemic injury, to the patient's brain nevertheless indicates a reasonable probability of the brain to recover from such injury, treatment decisions can be made to provide further interventional treatment. The measure of aggregate ischemic exposure, or ischemic injury, can for example be based upon an assessment of whether the cerebral tissue oxygenation level of the patient was above a certain threshold level for at least a certain threshold percentage of the elapsed resuscitation effort.

At 902, $rSO_2$ data can be received. Such $rSO_2$ data can provide a measure of the balance of supply and demand of oxygen in the brain tissues. At 904, the $rSO_2$ data can be analyzed relative to time. The duration of $rSO_2$ levels and changes in $rSO_2$ levels can be indicative of oxygen supply and/or demand to/of the patient's brain. At 906, a determination of the measure of the ischemic injury to the patient's brain can be made. The determination can be based on the treatment session to that point and cerebral tissue oxygenation levels during that time. For example, the determination can be made that the cerebral tissue oxygenation level of the patient was above a level for at least a percentage of the treatment session, and as such the measure of ischemic injury is a first value based on the collected cerebral tissue oxygenation data during the treatment session. Various cerebral tissue oxygenation level and percentage of treatment session associations can be used to determine the measure of ischemic injury at 906. Such determination can be made on the received $rSO_2$ data for the patient, other received patient physiological parameter data, and/or, optionally, outcome and $rSO_2$ data from other patients. The outcome and $rSO_2$ data for other patients can be collected and analyzed to refine the model, process and/or algorithm used in determining the measure of the ischemic injury to the patient's brain. In this manner, the determination accuracy can be further refined and updated, such as in response to new and/or updated patient interventions and/or treatments. Along with the outcome and $rSO_2$ data, other physiological parameter and/or patient data can be collected for analysis and/or correlation to assist with refining the determination. Optionally, the determination at 906 can be indeterminate. The indeterminate determination can be indicative that the cerebral tissue oxygenation data of the patient is not sufficient and that other physiological data should be used to determine the measure of ischemic injury.

Figure 10:
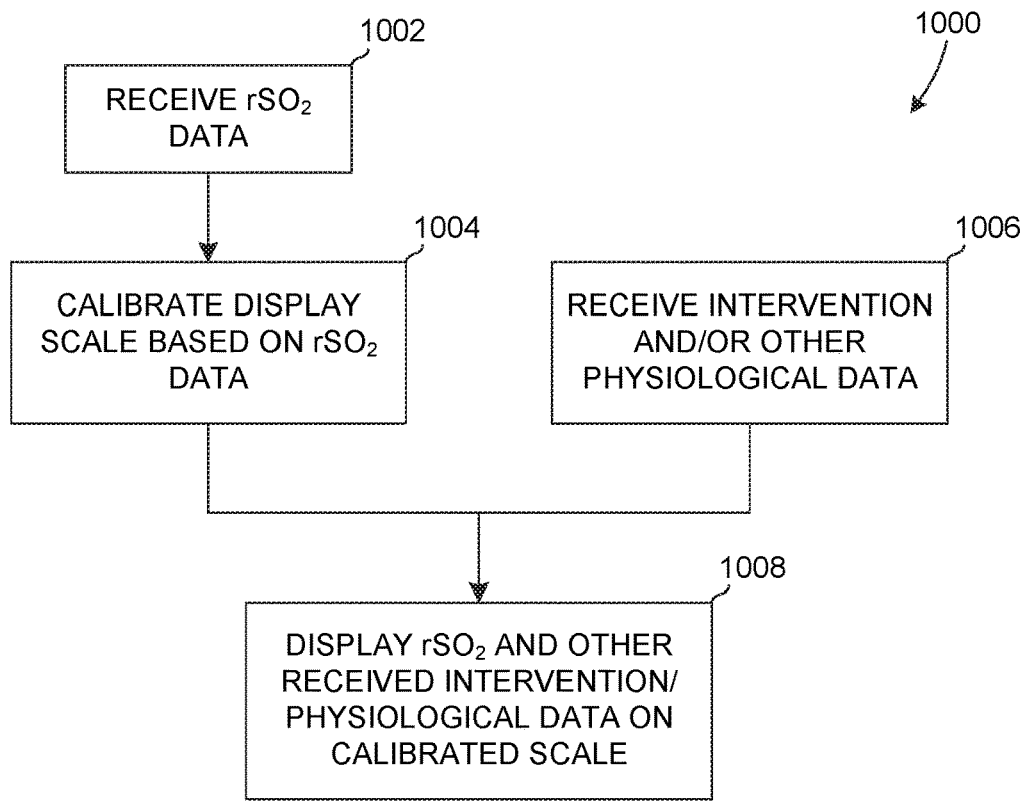
FIG. 10 is still another example physiological feedback method.

FIG. 10 is a method 1000 for presenting cerebral and/or other tissue oximetry, such as $rSO_2$, and/or other capnography/oximetry data, in conjunction with other patient information to assist with patient monitoring and/or treatment. Such display can assist with determining cause-and-effect relationships between treatments and/or interventions and a patient's physiological response to the same.

At 1002, $rSO_2$ data can be received. At 1004, a display scale can be calibrated based on the $rSO_2$ data. Calibration of the display can include calibration based on a timing, such as sampling rate, of the $rSO_2$ data and/or a magnitude, such as levels/percentage, of the $rSO_2$ data. In an example, the calibration of the display can include condensing the time scale in order to display a history of events that occur on a minute time scale, such as changes and/or initiation of treatments/interventions, rather than a second-to-second time scale as might be used to collect $rSO_2$, and/or other physiological, data. At 1006, intervention data, such as changes to treatment and/or initiation of treatment, and other physiological data, such as other capnography and/or oximetry data, can be received. Changes to treatment can include changes to CPR administration, such as changes to compression rate and/or depth, and can include changes to ventilation of the patient. Additionally, or alternatively, the changes to treatment can include the administration of medication and/or other treatments such as defibrillation shocks. At 1008, the $rSO_2$ and the received intervention/physiological data can be presented on the calibrated scale of the display. The display of such information can allow a user treating the patient to determine the effect of treatment and/or treatment changes on the physiological state of the patient, such as an improvement or decline in the patient's physiological state. The display can provide information that can assist with further treatment and/or monitoring of the patient.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be used for realizing the invention in diverse forms thereof.

The invention claimed is:

1. A medical device, comprising:
    a processor configured to:
        receive physiological parameter data comprising measurements of physiological parameters of a patient,
        determine an effectiveness index based at least in part on a positive correlation between the physiological parameters in the physiological parameter data, the effectiveness index being indicative of a hemodynamic adequacy of the patient;
        generate an instruction to alter a treatment of the patient based at least in part on the effectiveness index; and
        output the instruction.

2. The medical device of claim 1, wherein the measurements comprise transthoracic impedance measurements, electrocardiogram (ECG) measurements, blood pressure measurements, blood flow measurements, cardiac performance measurements, or cardiopulmonary resuscitation (CPR) measurements.

3. The medical device of claim 1, wherein the processor is further configured to receive confounder data and to output the confounder data.

4. The medical device of claim 3, wherein the confounder data indicates an administration of a medication to the patient, an observation of a behavior of the patient, or an administration of the treatment to the patient.

5. The medical device of claim 1, wherein the processor is further configured to receive confounder data and to determine the effectiveness index based at least in part on the confounder data.

6. The medical device of claim 1, wherein the processor is further configured to iteratively determine the effectiveness index.

7. The medical device of claim 1, wherein the physiological parameter data comprises oxygenation data, and
    wherein the processor is further configured to calculate an oxygenation trend based at least in part on the oxygenation data and to determine the effectiveness index based at least in part on the oxygenation trend.

8. The medical device of claim 7, wherein the processor is further configured to identify a trajectory of the oxygenation trend and to determine the effectiveness index based at least in part on the trajectory.

9. The medical device of claim 8, wherein the processor is further configured to identify, based at least in part on the trajectory, a return of spontaneous circulation (ROSC) of the patient, a likelihood of ROSC of the patient, or a re-arrest of the patient.

10. The medical device of claim 1, wherein the processor is further configured to calculate a physiological parameter trend based at least in part on the physiological parameter data and to determine the effectiveness index based at least in part on the physiological parameter trend.

11. The medical device of claim 1, wherein the processor is further configured to identify, based at least in part on the effectiveness index, a return of spontaneous circulation (ROSC) of the patient, a likelihood of ROSC of the patient, or a re-arrest of the patient.

12. The medical device of claim 1, wherein the processor outputs the instruction by transmitting the instruction to a display.

13. The medical device of claim 1, wherein the processor is further configured to transmit the effectiveness index to a computing device.

14. A medical device, comprising:
    multiple patient sensors configured to generate physiological parameter data by measuring respective multiple physiological parameters of a patient, the multiple patient sensors comprising an oxygenation sensor that is configured to sense tissue oximetry measurements of the patient or an airway $CO_2$ sensor configured to sense capnography measurements of the patient;
    a processor electrically coupled to the multiple patient sensors and configured to receive the physiological parameter data, the processor further configured to:
        determine an effectiveness index based at least in part on a positive correlation between the physiological parameters in the physiological parameter data, the effectiveness index being indicative of a hemodynamic adequacy of the patient;
        generate an instruction to alter a treatment of the patient based at least in part on the effectiveness index; and
        output the instruction.

15. The medical device of claim 14, wherein the processor is further configured to receive confounder data indicating an administration of a medication to the patient, an observation of a behavior of the patient, or an administration of the treatment to the patient and to determine the effectiveness index based at least in part on the confounder data.

16. The medical device of claim 14, wherein the processor is further configured to calculate a physiologic trend based on the tissue oximetry measurements or the capnography measurements and to determine the effectiveness index based at least in part on the physiologic trend.

17. The medical device of claim 16, wherein the processor is further configured to identify a trajectory of the physiologic trend and to determine the effectiveness index based at least in part on the trajectory.

18. The medical device of claim 14, wherein the processor is further configured to identify, based at least in part on the effectiveness index, a return of spontaneous circulation (ROSC) of the patient, a likelihood of ROSC of the patient, or a re-arrest of the patient.

19. A method, comprising:
    generating, by multiple sensors, physiological parameter data comprising oxygenation measurements of a patient and $CO_2$ measurements of the patient,
    determining, by a processor, an effectiveness index based at least in part on a positive correlation between the oxygenation measurements and the $CO_2$ measurements, the effectiveness index being indicative of a hemodynamic adequacy of the patient;

generating, by the processor, an instruction to alter a cardiopulmonary resuscitation (CPR) treatment of the patient based at least in part on the effectiveness index; and outputting, by a display, the instruction and the effectiveness index.

20. The method of claim 19, further comprising:

identifying, by the processor and based at least in part on the effectiveness index, a return of spontaneous circulation (ROSC) of the patient; and outputting, by the display, an alert indicating the ROSC.

* * * * *